United States Patent [19]

Zimmerman

[11] Patent Number: 4,643,761
[45] Date of Patent: Feb. 17, 1987

[54] HERBICIDAL SULFONAMIDES

[75] Inventor: William T. Zimmerman, Landenberg, Pa.

[73] Assignee: E. I. Du Pont De Nemours and Company, Wilmington, Del.

[21] Appl. No.: 695,605

[22] Filed: Jan. 28, 1985

[51] Int. Cl.$^4$ .................. C07D 239/47; A01N 47/36
[52] U.S. Cl. ........................................ 71/92; 544/321
[58] Field of Search ............................ 544/321; 71/92

[56] References Cited

U.S. PATENT DOCUMENTS 4,378,991 4/1983 Levitt ..................................... 71/93
4,474,600 10/1984 Aya et al. ............................. 71/92

*Primary Examiner*—Robert Gerstl

[57] ABSTRACT

Specific halogenated phenylbenzenesulfonamide compounds such as 2-chloro-N-[(4,6-dimethoxypyridmin-2-yl) aminocarbonyl]-6-phenylbenzenesulfonamide and 2-chloro-N-[(4-methoxy-6-methylpyrimidin-2-yl)aminocarbonyl]-6-phenylbenzenesulfonamide display excellent herbicidal utility for the selective control of weeds in rice.

28 Claims, No Drawings

HERBICIDAL SULFONAMIDES

BACKGROUND OF THE INVENTION

U.S. Pat. No. 4,378,991, issued Apr. 5, 1983 to Levitt discloses benzenesulfonamide compounds which display herbidical activity of the formula

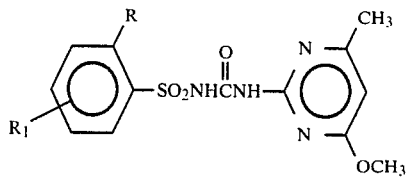

wherein R, among other values, can be phenyl, optionally substituted, and $R_1$ can be H, F, Cl, Br, $NO_2$, $CF_3$, $C_1$-$C_4$ alkyl, $OCF_3$ or $C_1$-$C_4$ alkoxy. While the disclosure of this reference generically encompasses the compounds of the present invention, neither the specific compounds of this invention nor their unexpected herbicidal utility for the selective control of weeds in rice, are taught therein.

SUMMARY OF THE INVENTION

This invention relates to novel compounds of Formula 1, agriculturally suitable compositions containing them and their method-of-use as selective preemergent and/or postemergent herbicides with excellent utility for the selective control of weeds in rice.

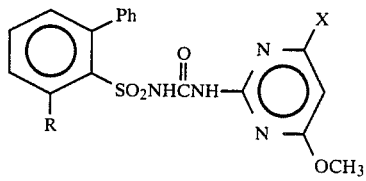

wherein
R is F, Cl or Br; and
X is $CH_3$ or $OCH_3$.

The specific compounds within the scope of this invention are:
- 2-chloro-N-[(4,6-dimethoxypyrimidin-2-yl)aminocarbonyl]-6-phenylbenzenesulfonamide;
- 2-chloro-N-[(4-methoxy-6-methylpyrimidin-2-yl)aminocarbonyl]-6-phenylbenzenesulfonamide;
- 2-fluoro-N-[(4,6-dimethoxypyrimidin-2-yl)aminocarbonyl]-6-phenylbenzenesulonamide;
- 2-fluoro-N-[(4-methoxy-6-methylpyrimidin-2-yl)aminocarbonyl]-6-phenylbenzenesulfonamide;
- 2-bromo-N-[(4,6-dimethoxypyrimidin-2-yl)aminocarbonyl]-6-phenylbenzenesulfonamide; and
- 2-bromo-N-[(4-methoxy-6-methylpyrimidin-2-yl)aminocarbonyl]-6-phenylbenzenesulfonamide.

These compounds display excellent preemergent and/or postemergent herbicidal utility and are especially useful for the selective control of weeds in rice.

DETAILED DESCRIPTION OF THE INVENTION

Synthesis

The compounds of Formula 1 can be prepared by the reaction of a 3-halobiphenyl-2-sulfonylisocyanate of Formula 2 with the appropriate pyrimidin-2-amine 3 as shown in Equation 1.

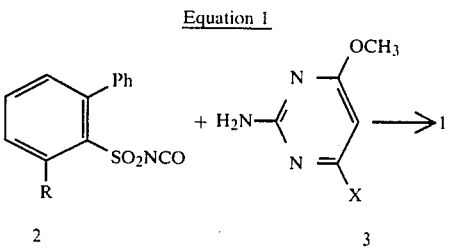

The reaction of Equation 1 is most successful when performed in an inert dipolar aprotic solvent such as methylene chloride, tetrahydrofuran or acetonitrile at temperatures between 20° and 80° C. A catalytic amount of 1,4-diazabicyclo[2.2.2]octane (DABCO) may be used to accelerate the reaction. In cases where the products are insoluble in the reaction solvent, isolation may be performed by simple filtration; when the products are soluble, isolation may be performed by evaporation of the solvent, trituration with a solvent such as 1-chlorobutane, diethyl ether or methanol and filtration.

2-Biphenylsulfonylisocyanates of Formula 2 can be prepared from sulfonamides of Formula 4 by methods described in U.S. Pat. No. 4,378,991, as indicated in Equation 2a. Alternatively, these sulfonylisocyanates can be synthesized via a two-step procedure, consisting of (1) reacting sulfonamide 4 with n-butylisocyanate in the presence of one molar equivalent of a base such as potassium carbonate in a solvent such as 2-butanone or acetonitrile, to form n-butylsulfonylureas of Formula 5 and (2) reaction of 5 with phosgene using DABCO as a catalyst in refluxing xylene as solvent. This method is similar to the preparation found in "Newer Methods of Preparative Organic Chemistry,", Forest, W., Ed., Vol. VI, Academic Press, NY, 1967, pp. 223–241. Equation 2b illustrates the procedure.

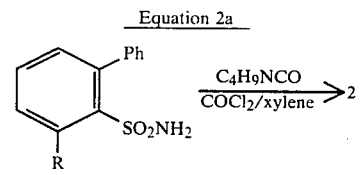

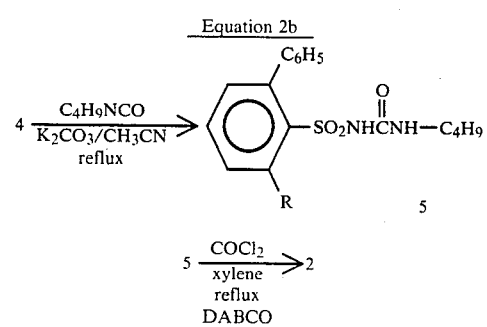

The compounds of Formula 1 also are available by the methodology described in South African Application No. 830441 and illustrated by Equation 3. Biphenylsulfonamides of Formula 4 react with pyrimidine carbamates of Formula 6 in 1,4-dioxane or acetonitrile at 20° to 80° C. for periods of 1 to 24 hours in the presence of one equivalent of 1,8-diazabicyclo[5.4.0]undec-5-ene (DBU). The resultant products are isolated by dilution of the reaction mixture with water, acidification and subsequent filtration. Heterocyclic arbamates of Formula 6 in turn are synthesized by reaction of pyrimidin-2-amines of Formula 3 with diphenyl carbonate or phenyl chloroformate in pyridine at temperatures ranging from 20° to 80° C., as indicated in Equation 3a.

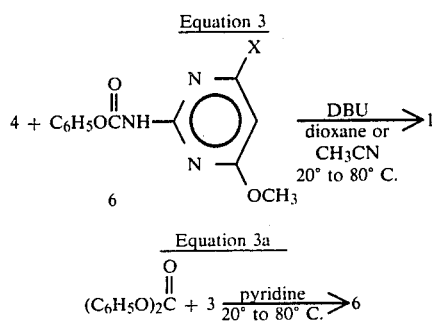

The synthesis of biphenylsulfonamide intermediates of Formula 4 may be accomplished as shown in Equation 4, wherein R is fluoro, chloro or hydrogen, and Z is iodo or bromo.

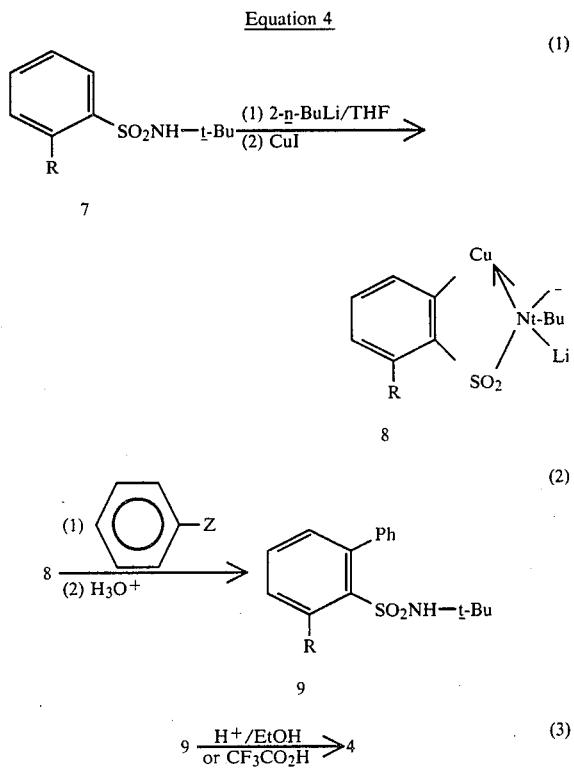

The copper compounds of Formula 8 are prepared by reacting the corresponding dilithio species with cuprous iodide in an inert aprotic solvent such as diethyl ether or tetrahydrofuran optionally in the presence of pyridine or quinoline. This dilithio intermediate is readily formed upon treatment of a N-t-butylsulfonamide of Formula 1 with two equivalents of n-butyllithium at 0° to 30° C. Treatment of the aryl copper intermediate 8 with phenyl iodide or bromide for 2 to 24 hours at 30° to 80° C. followed by addition of aqueous acid affords the biphenylsulfonamides 9. The experimental procedures are related to those presented in the following references: F. E. Zwiegler, et al., *J. Am. Chem. Soc.*, 102, 790 (1980); M. Nilsson and C. Ullenius, *Acta Chem. Scand.*, 24, 2379 (1974). Removal of the N-t-butyl protecting group is accomplished by heating sulfonamides 9 in alcohol with an acid catalyst or by treatment with trifluoroacetic acid to afford sulfonamides of Formula 4.

For the sulfonamide of Formula 4 in which R is bromo, the following alternative sequence is preferable as shown in Equation 5.

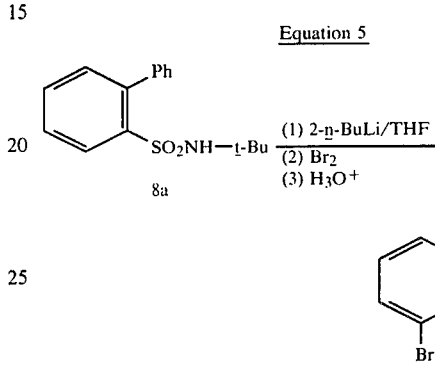

The biphenylsulfonamide, 8a, prepared as described above, is treated with 2 equivalents of an organolithium base such as n-butyllithium in an inert solvent such as tetrahydrofuran, followed by treatment wih bromine preferably at low temperatures (−60° to −80° C.). Treatment of the reaction mixture with aqueous acid affords the bromobiphenylsulfonamide 9a.

The synthesis of herbicidal sulfonylureas of Formula 1 is further demonstrated in the following examples, wherein temperatures are in °C.

EXAMPLE 1

2-Chloro-N-(1,1-dimethylethyl)-6-phenylbenzenesulfonamide

A solution of 21.5 g (0.087 mol) 2-chloro-N-t-butylbenzenesulfonamide in anhydrous tetrahydrofuran was cooled to −30° under a nitrogen atmosphere while 121 ml of 1.6M n-butyllithium in hexanes was added over ten minutes. The mixture was then stirred for one hour at room temperature then recooled to below 0° and 16.6 g (0.087 mol) cuprous iodide (Alfa ultrapure grade) was added. After ten minutes at 0°, 10 ml (0.089 mol) iodobenzene was added and the mixture heated to reflux for 18 hours. The suspension was subsequently cooled to below 15° and 20 ml of acetic acid was added followed by 400 ml each of ethyl acetate and concentrated ammonium hydroxide. After stirring vigorously in air for 15 minutes the mixture was filtered, rinsed with water and ethyl acetate and the filtrate separated. The blue aqueous phase was extracted with 200 ml ethyl acetate and the combined organic phase washed successively with 200 ml concentrated ammonium hydroxide, water and brine, then dried and evaporated in vacuo. The solid residue was triturated with ether and collected by filtration to afford 23.5 g (84%) of the title compound, m.p. 168°–170°. An NMR spectrum (90 MHz) in CDCl₃ had resonances at 1.10 (s, 9H), 5.08 (s, br, NH), 7.35–7.65 (m, ArH, 8H) ppm.

EXAMPLE 2

2-Chloro-6-phenylbenzenesulfonamide

A solution of 2-chloro-N-(1,1-dimethylethyl)-6-phenylbenzenesulfonamide (23 g, 0.071 mol) in a mixture of 120 ml trifluoroacetic acid (TFA) plus 4 ml water was heated to reflux for 2 hours. The TFA was evaporated in vacuo and the residue partitioned between methylene chloride and water. The organic layer was dried (MgSO₄), evaporated, and the residue crystallized from ether/methylene chloride to afford 15.9 g of crystalline solid in two crops, m.p. 185°–87°. NMR (90 MHZ, CDCl₃) 6.45 (s, br, NH₂). 7.3–7.7 (m, 8H) ppm.

EXAMPLE 3

N-(Butylaminocarbonyl)-2-chloro-6-phenylbenzenesulfonamide

A mixture of 7.7 g (0.029 mol) 2-chloro-6-phenylbenzenesulfonamide, 3.6 ml (0.032 mol) n-butylisocyanate and 4.1 g (0.03 mol) potassium carbonate was heated in 80 ml dry acetonitrile for 18 hours at reflux. The solvent was evaporated and the residue treated with 1N HCl and ethyl acetate and the insoluble solids were collected, washed with water and then ether. Additional material was obtained from the organic phase of the filtrate to afford a total of 10 g of the title compound, m.p. 184°–186°. NMR (90 MHz, CDCl₃), 0.9 (CH₃, t, br), 1.4 (4H, m), 3.05 (q, J=7 Hz, 2H), 5.9 (t, br, NH), 7.2–7.6 (m, 8H) ppm.

EXAMPLE 4

2-Chloro-6-phenylbenzenesulfonyl Isocyanate

A mixture of 9.5 g (0.026 mol) of N-(butylaminocarbonyl)-2-chloro-6-phenylbenzenesulfonamide of Example 3 and 0.02 g DABCO was heated in 120 ml dry xylenes to reflux (138°) with a short water condenser and dry ice cold finger condenser attached. An excess of phosgene gas was introduced and reflux was continued for 2 hours. The mixture was then cooled, filtered under nitrogen atmosphere then evaporated to an amber oil, 8.5 g. An infrared spectrum exhibited an absorption at 2250 cm⁻¹ indicating the title compound.

EXAMPLE 5

2-Chloro-N-[4-methoxy-6-methylpyrimidin-2-yl)aminocarbonyl]-6-phenylbenzenesulfonamide A solution of 8.5 g (0.026 mol) of the isocyanate of Example 4 in 80 ml dry acetonitrile was treated with 3.1 g (0.022 mol) 4-methoxy-6-methylpyrimidin-2-amine then stirred for 20 hours at ambient temperature. The solids which crystallized were collected to afford 7.6 g of the title compound in two crops, m.p. 181°–185° dec. IR(nujol) 1705, 3200 NH (sh) cm⁻¹; NMR (90 MHz, CDCl₃), 2.35 (s, 3H), 3.90 (s, 3H), 6.29 (s, 1H), 7.2–7.7 (m, 9H), 12.8 (s, br, 1H) ppm.

Using the techniques described in Examples 1 though 5 and in the preceding summary, the compounds of Table 1 may be prepared.

TABLE 1

| R | X | m.p. (°C.) |
|---|---|---|
| F | CH₃ | |
| Cl | CH₃ | 181–185 dec. |
| Br | CH₃ | |
| F | OCH₃ | |
| Cl | OCH₃ | 194–198 dec. |
| Br | OCH₃ | |

Formulations

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid inert diluent(s). More specifically, they will contain these ingredients in the following approximate proportions:

TABLE 2

| | Weight Percent* | | |
|---|---|---|---|
| | Active Ingredient | Diluent(s) | Surfactant(s) |
| Wettable Powders | 20–90 | 0–74 | 1–10 |
| Oil Suspensions, Emulsions, Solutions, (including Emulsifiable Concentrates) | 3–50 | 40–95 | 0–15 |
| Aqueous Suspension | 10–50 | 40–84 | 1–20 |
| Dusts | 1–25 | 70–99 | 0–5 |
| Granules and Pellets | 0.1–95 | 5–99.9 | 0–15 |
| High Strength Compositions | 90–99 | 0–10 | 0–2 |

*Active ingredient plus at least one of a Surfactant or a Diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J., but other solids, either mined or manufactureed, may be used. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid composition are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", Chemical Engineering, Dec. 4, 1967, pp. 147ff, and "Perry's Chemical Engineer's Handbook", 5th Ed., McGraw-Hill, N.Y., 1973, pp. 8–57ff.

In the following examples, all parts are by weight unless otherwise indicated.

EXAMPLE 6

Wettable Powder 2-chloro-N-[(4,6-dimethoxypyrimidin-2-yl)aminocarbonyl]-6-phenylbenzenesulfonamide: 50%
sodium alkylnaphthalenesulfonate: 2%
low viscosity methyl cellulose: 2%
diatomaceous earth: 46%

The ingredients are blended, coarsely hammer-milled and then air-milled to produce particles essentially all below 50 microns in diameter. The product is reblended before packaging.

EXAMPLE 7

Granule

Wettable Powder of Example 6: 5%
attapulgite granules (U.S.S. 20–40 mesh; 0.84–0.42 mm): 95%

A slurry of wettable powder containing 25% solids is sprayed on the surface of attapulgite granules in a double-cone blender. The granules are dried and packaged.

EXAMPLE 8

Extruded Pellet 2-chloro-N-[(4-methoxy-6-methylpyrimidin-2-yl)aminocarbonyl]-6-phenylbenzenesulfonamide: 25%
anhydrous sodium sulfate: 10%
crude calcium ligninsulfonate: 5%
sodium alkylnaphthalenesulfonate: 1%
calcium/magnesium bentonite: 59%

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 9

Low Strength Granule 2-fluoro-N-[(4,6-dimethoxypyrimidin-2-yl)aminocarbonyl]-6-phenylbenzenesulfonamide: 1%
N,N-dimethylformamide: 9%
attapulgite granules (U.S.S. 20–40 sieve): 90%

The active ingredient is dissolved in the solvent and the solution is sprayed upon dedusted granules in a double cone blender. After spraying of the solution has been completed, the blender is allowed to run for a short period and then the granules are packaged.

EXAMPLE 10

Aqueous Suspension 2-chloro-N-[(4,6-dimethoxypyrimidin-2-yl)aminocarbonyl]-6-phenylbenzenesulfonamide: 40%
polyacrylic acid thickener: 0.3%
dodecylphenol polyethylene glycol ether: 0.5%
disodium phosphate: 1%
monosodium phosphate: 0.5%
polyvinyl alcohol: 1.0%
water: 56.7%

The ingredients are blended and ground together in a sand mill to produce particles essentially all under 5 microns in size.

EXAMPLE 11

Oil Suspension 2-chloro-N-[(4-methoxy-6-methylpyrimidin-2-yl)aminocarbonyl]-6-phenylbenzenesulfonamide: 35%
blend of polyalcohol carboxylic esters and oil soluble petroleum sulfonates: 6%
xylene: 59%

The ingredients are combined and ground together in a sand mill to produce particles essentially all below 5 microns. The product can be used directly, extended with oils, or emulsified in water.

EXAMPLE 12

Granule 2-chloro-N-[(4-methoxy-6-methylpyrimidin-2-yl)aminocarbonyl]-6-phenylbenzenesulfonamide: 80%
wetting agent: 1%
crude ligninsulfonate salt (containing 5–20% of the natural sugars): 10%
attapulgite clay: 9%

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14–100 mesh (1410–149 microns), and packaged for use.

EXAMPLE 13

High Strength Concentrate 2-fluoro-N-[(4,6-dimethoxypyrimidin-2-yl)aminocarbonyl]-6-phenylbenzenesulfonamide: 99%
silica aerogel: 0.5%
synthetic amorphous silica: 0.5%

The ingredients are blended and ground in a hammer-mill to produce a material essentially all passing a U.S.S. No. 50 screen (0.3 mm opening). The concentrate may be formulated further if necessary.

EXAMPLE 14

Wettable Powder 2-chloro-N-[(4,6-dimethoxypyrimidin-2-yl)aminocarbonyl]-6-phenylbenzenesulfonamide: 90%
dioctyl sodium sulfosuccinate: 0.1%
synthetic fine silica: 9.9%

The ingredients are blended and ground in a hammermill to produce particles essentially all below 100 microns. The material is sifted through a U.S.S. No. 50 screen and then packaged.

EXAMPLE 15

Wettable Powder 2-bromo-N-[(4,6-dimethoxypyrimidin-2-yl)aminocarbonyl]-6-phenylbenzenesulfonamide: 40%
sodium ligninsulfonate: 20%
montmorillonite clay: 40%

The ingredients are thoroughly blended, coarsely hammer-milled and then air-milled to produce particles essentially all below 10 microns in size. The material is reblended and then packaged.

EXAMPLE 16

Dust 2-bromo-N-[(4-methoxy-6-methylpyrimidin-2-yl)aminocarbonyl]-6-phenylbenzenesulfonamide: 10%
attapulgite: 10%
talc: 80%

The active ingredient is blended with attapulgite and then passed through a hammer-mill to produce particles substantially all below 200 microns. The ground concentrate is then blended with powdered pyrophyllite until homogeneous.

Utility

The compounds of this invention are particularly useful for the control of weeds in rice. They may be used for both paddy and dryland rice. They may be applied postemergence to dryland rice, to paddy rice or to rice from which the flood has been removed. The flood may be restored when the chemical has had time to penetrate the weeds. They may also be applied to paddy rice after transplanting as a spray or granule. The application may be made from 3 to 10 days after transplanting or from three days before seeding to 7 days after seeding.

The compounds of this invention may be used in combination with other rice herbicides including thiobencarb (S-(4-chlorophenyl)methyldiethylcarbamothioate), butachlor (2-chloro-2',6'-diethyl-N-(butoxymethyl)acetanlide), propanil (3,4-dichlorophenylpropionanilide), and MY 93 (S-(1-methyl-1-phenethyl)-piperidine-1-carbathioate.

Rates of 4 to 100 g/Ha will provide weed control. The compounds are particularly useful for the control of a variety of weeds in rice, including *Echinochloa cru-sqalli, Cyperus difformis*, Scirpus, Eleocharis, and Sagittaria species.

Compounds

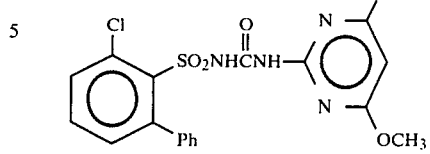

Compound A

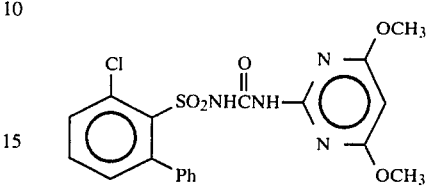

Compound B

Test A

Japonica and Indica Rice (2.5 leaf stage) seedlings were transplanted into 15 cm diam. wax cups containing a sandy loam soil. Compounds, formulated in a nonphytotoxic solvent, were applied 3 to 5 days after transplanting directly to the paddy water (3.0 cm deep). Rice injury was evaluated 14 to 21 days after treatment by measuring seedling fresh weight. Data were converted to a percent injury rating compared to an untreated control. The results of the test are shown in Table A.

TABLE A

| Rate (g/ha)   | 0.25 | 1  | 4  | 16 | 63 | 250 | 1000 |
| ------------- | ---- | -- | -- | -- | -- | --- | ---- |
| Compound A    |      |    |    |    |    |     |      |
| Japonica Rice | 0    | 0  | 0  | 10 | 10 | 35  | 50   |
| Indica Rice   | 0    | 0  | 0  | 40 | 0  | 20  | 25   |
| Compound B    |      |    |    |    |    |     |      |
| Japonica Rice | 0    | 0  | 0  | 0  | 40 | 40  | 60   |
| Indica Rice   | 25   | 25 | 25 | 0  | 35 | 40  | 60   |

Test B

Sixteen-cm diameter Wagner pots, equipped with a stoppered drain opening near the bottom of the side wall, were partially filled with Woodstown sandy loam. About 1500 ml of water were added to each pot to bring the water level to a point 3 cm above the soil surface. Japonica and Indica rice seedlings were transplanted as described in Test A. Also, a number of barnyardgrass (*Echinochloa crusgalli*) seeds were added to each pot. At the same time, seedlings or tubers of the following species were transplanted into the muddy soil: water plaintain (*Alisma trivale*), Scirpus (*Scirpus mucronatus*), and Cyperus (*Cyperus difformis*). The weed species selected for this test are of economic importance in major rice-growing areas. The chemical treatments were applied as described in Test A, within hours after transplanting of two additional species: water chestnut (Eleocharis spp.) and arrowhead (*Sagitarria latifolia*). Shortly after treatment, the drain hole was opened to drop the water level by 2 cm. Water was then added to restore the water level to its original height. The following day the draining and refilling process was repeated. The pots were then maintained in the greenhouse. Rates of application and plant response ratings made 21 days after treatment are summarized in Table B.

Plant response was visually assessed using a rating system of 100%=complete plant death and 0%=no control or injury.

TABLE B

| | Plant Response Ratings[1] | | | |
|---|---|---|---|---|
| | Compound A | | Compound B | |
| Rate (g/ha) | 125 | 30 | 8 | 30 |
| Japonica Rice | 10 | 0 | 0 | 0 |
| Indica Rice | 0 | 0 | 0 | 0 |
| Barnyardgrass | 100 | 95 | 25 | 50 |
| Water Chestnut | 100 | 95 | 25 | 50 |
| Arrowhead | 100 | 95 | 0 | 50 |
| Scirpus | 100 | 100 | 0 | 80 |
| Cyperus | 100 | 95 | 0 | 75 |
| Water Plaintain | 100 | 100 | 50 | 90 |

[1] 0 = no injury, 100 = complete control

Test C

The test is conducted in Wagner pots as described in Test B. Rice (Japoninca and Indica) is transplanted at the 2.5 leaf stage into one Wagner pot and weeds in a second pot. *Monochoria vaginalis* was included in this test, in addition to weeds listed in Test B. Compounds, formulated in a non-phytotoxic solvent, are applied directly the paddy water (3.0 cm depth) 4 to 6 days after transplanting. Visual evaluation is conducted 21 to 25 days after treatment using a 0 to 100% scale, where 0=no weed control or rice injury and 100=complete death of the plant. Results are shown in Table C.

TABLE C

| | Compound A | | | |
|---|---|---|---|---|
| Rate (g/ha) | 125 | 63 | 30 | 16 |
| Japonica Rice | 20 | 0 | 0 | 0 |
| Indica Rice | 20 | 20 | 0 | 0 |
| Barnyardgrass | 100 | 95 | 95 | 95 |
| Water Chestnut | 90 | 95 | 80 | 85 |
| Arrowhead | 100 | 90 | 75 | 85 |
| Scirpus | 95 | 95 | 90 | 70 |
| Cyperus | 100 | 95 | 70 | 75 |
| Monchloria | 100 | 100 | 100 | 90 |

Test D

Tests are also conducted on direct seeded rice. Pregerminated Indica rice seeds are sown into the Wagner pots containing saturated soil. A corresponding Wagner pot is seeded with barnyardgrass and hemp sesbania. Compounds are applied prior to flooding (3 to 4 days after seeding) and after flooding to 3.0 cm (7 to 10 days after seeding). Visual evaluation is conducted as described above. The results are shown in Table D. Plant response ratings are the same as those described for Test C.

TABLE D

| | Compound A | | | |
|---|---|---|---|---|
| Rate (g/ha) | 125 | 63 | 30 | 16 |
| Pre Flood | | | | |
| Indica Rice | 20 | 10 | 0 | 0 |
| Barnyardgrass | 95 | 95 | 90 | 90 |
| Sesbania | 100 | 100 | 100 | 100 |
| Post Flood | | | | |
| Indica Rice | 25 | 0 | 0 | 0 |
| Barnyardgrass | 95 | 80 | 80 | 80 |
| Sesbania | 100 | 100 | 100 | 100 |

Test E

Seeds of rice (*Oryza sativa*), barnyardgrass (*Echinochloa crusgalli*), morningglory (*Ipomoea purpurea*), wild oats (*Avena fatua*), nutsedge (*Cyperus rotundus*), and crabgrass (*Digitaria ischaemum*) were sown in 25 cm diameter plastic pots containing Sassafras sandy loam soil. Compounds, formulated in a non-phytotoxic solvent, were applied as preemergence and postemergence (rice=2 to 3 leaves) treatments. Evaluation, by visual assessment, was conducted 21 to 25 days following treatment. Weed control and rice injury ratings were based on a percent injury system relative to the untreated controls. The results are summarized in Table E.

TABLE E

| | | Plant Response Ratings[1] | | | | | |
|---|---|---|---|---|---|---|---|
| | g/ha | Indica Rice | Barnyardgrass | Nutsedge | Morningglory | Wild Oats | Crabgrass |
| Postemergence | | | | | | | |
| Cmpd. A | 32 | 0 | 25 | 0 | 35 | 0 | 0 |
| | 64 | 0 | 75 | 0 | 40 | 0 | 0 |
| | 125 | 0 | 80 | 0 | 80 | 20 | 0 |
| | 250 | 0 | 85 | 70 | 95 | 50 | 20 |
| Cmpd. B | 32 | 0 | 0 | 0 | 50 | 0 | 0 |
| | 64 | 0 | 0 | 0 | 65 | 0 | 0 |
| | 125 | 0 | 0 | 0 | 85 | 0 | 0 |
| | 250 | 0 | 0 | 70 | 85 | 0 | 20 |
| Preemergence | | | | | | | |
| Cmpd. A | 32 | 0 | 40 | 0 | 0 | 0 | 0 |
| | 64 | 0 | 45 | 0 | 0 | 0 | 0 |
| | 125 | 0 | 75 | 0 | 0 | 0 | 0 |
| | 250 | 0 | 85 | 0 | 60 | 65 | 0 |
| Cmpd. B | 32 | 0 | 0 | 0 | 0 | 0 | 0 |
| | 64 | 0 | 0 | 0 | 0 | 0 | 0 |
| | 125 | 0 | 20 | 0 | 0 | 0 | 0 |
| | 250 | 0 | 20 | 0 | 0 | 0 | 0 |

[1] 0 = no injury, 100 = complete control

What is claimed is:

1. A compound of the formula

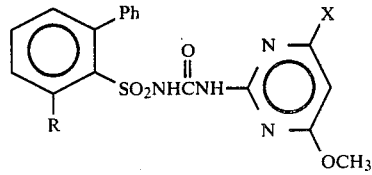

wherein
R is F, Cl or Br; and
X is $CH_3$ or $OCH_3$.

2. The compound of claim 1 which is 2-chloro-N-[(4,6-dimethoxyprimidin-2-yl)aminocarbonyl]-6-phenylbenzenesulfonamide.

3. The compound of claim 1 which is 2-chloro-N-[(4-methoxy-6-methylpyrimidin-2-yl)aminocarbonyl]-6-phenylbenzenesulfonamide.

4. The compound of claim 1 which is 2-fluoro-N-[(4,6-dimethoxypyrimidin-2-yl)aminocarbonyl]-6-phenylbenzenesulfonamide.

5. The compound of claim 1 which is 2-fluoro-N-[(4-methoxy-6-methylpyrimidin-2-yl)aminocarbonyl]-6-phenylbenzenesulfonamide.

6. The compound of claim 1 which is 2-bromo-N-[(4,6-dimethoxypyrimidin-2-yl)aminocarbonyl]-6-phenylbenzenesulfonamide.

7. The compound of claim 1 which is 2-bromo-N-[(4-methoxy-6-methylpyrimidin-2-yl)aminocarbonyl]-6-phenylbenzenesulfonamide.

8. A compositon suitable for controlling the growth of undesired vegetation in rice which comprises an effective amount of a compound of claim 1 and at least one of the following: surfactant, solid or liquid diluent.

9. A composition suitable for controlling the growth of undesired vegatation in rice which comprises an effective amount of a compound of claim 2 and at least one of the following: surfactant, solid or liquid diluent.

10. A composition suitable for controlling the growth of undesired vegetation in rice which comprises an effective amount of a compound of claim 3 and at least one of the following: surfactant, solid or liquid diluent.

11. A composition suitable for controlling the growth of undesired vegetation in rice which comprises an effective amount of a compound of claim 4 and at least one of the following: surfactant, solid or liquid diluent.

12. A composition suitable for controlling the growth of undesired vegetation in rice which comprises an effective amount of a compound of claim 5 and at least one of the following: surfactant, solid or liquid diluent.

13. A composition suitable for controlling the growth of undesired vegetation in rice which comprises an effective amount of a compound of claim 6 and at least one of the following: surfactant, solid or liquid diluent.

14. A composition suitable for controlling the growth of undesired vegetation in rice which comprises an effective amount of a compound of claim 7 and at least one of the following: surfactant, solid or liquid diluent.

15. A method for controlling the growth of undesired vegetation which comprises applying to the locus to be protected an effective amount of a compound of claim 1.

16. The method of claim 15 wherein said locus to be protected comprises rice.

17. A method for controlling the growth of undesired vegetation which comprises applying to the locus to be protected an effective amount of a compound of claim 2.

18. The method of claim 17 wherin said locus to be protected comprises rice.

19. A method for controlling the growth of undesired vegetation which comprises applying to the locus to be protected an effective amount of a compound of claim 3.

20. The method of claim 19 wherein said locus to be protected comprises rice.

21. A method for controlling the growth of undesired vegetation which comprises applying to the locus to be protected an effective amount of a compound of claim 4.

22. The method of claim 21 wherein said locus to be protected comprises rice.

23. A method for controlling the growth of undesired vegetation which comprises applying to the locus to be protected an effective amount of a compound of claim 5.

24. The method of claim 23 wherein said locus to be protected comprises rice.

25. A method for controlling the growth of undesired vegetation which comprises applying to the locus to be protected an effective amount of a compound of claim 6.

26. The method of claim 25 wherein said locus to be protected comprises rice.

27. A method for controlling the growth of undesired vegetation which comprises applying to the locus to be protected an effective amount of a compound of claim 7.

28. The method of claim 27 wherein said locus to be protected comprises rice.

* * * * *